United States Patent [19]

Crommelynck et al.

[11] 4,297,298

[45] Oct. 27, 1981

[54] METHOD OF PREPARING STABLE DILUTE SOLUTIONS OF ALIPHATIC CARBOXYLIC PERACIDS, AND THE RESULTING SOLUTIONS

[75] Inventors: François Crommelynck, Saint Martin Le Vinoux; Michel Granger, Chalon-sur-Saone; Michel Rio, Elancourt; Jacques Tourdot, Paris, all of France

[73] Assignee: L'Air Liquide, Societe Anonyme pour l'Etude Procedes Georges Claude, Paris, France

[21] Appl. No.: 171,047

[22] Filed: Jul. 22, 1980

[30] Foreign Application Priority Data

Aug. 1, 1979 [FR] France .............................. 79 19761

[51] Int. Cl.³ ........................................... C07C 279/10
[52] U.S. Cl. ............................ 260/502 R; 260/502 A; 568/559
[58] Field of Search ....................... 260/502 R, 502 A; 568/559; 252/186

[56] References Cited

U.S. PATENT DOCUMENTS

| 3,192,254 | 6/1965 | Hayes | 260/502 R |
| 3,432,546 | 6/1969 | Oringer et al. | 260/502 R |
| 4,051,058 | 9/1977 | Bowing et al. | 252/186 |
| 4,051,059 | 9/1977 | Bowing et al. | 252/186 |
| 4,087,454 | 5/1978 | Prescher et al. | 260/502 R |
| 4,088,679 | 5/1978 | Prescher et al. | 260/502 R |

FOREIGN PATENT DOCUMENTS

| 1352479 | 5/1974 | France | 260/502 R |
| 2321301 | 3/1977 | France | . |

OTHER PUBLICATIONS

Greenspan, "J. Amer. Chem. Soc.", vol. 46, p. 907 (1946).

*Primary Examiner*—Werren B. Lone
*Attorney, Agent, or Firm*—Browdy and Neimark

[57] ABSTRACT

The invention relates to the preparation of dilute solutions of aliphatic carboxylic peracids.

In a first step, a concentrated solution of aliphatic peracid is prepared from the corresponding acid or anhydride and concentrated hydrogen peroxide in the presence of a strong acid catalyst, preferably the minimum quantity necessary for obtaining equilibrium in the system within 48 hours; and in a second step, the concentrated solution of aliphatic peracid is diluted with a solution containing at least one of the reagents, so as to bring the concentration of aliphatic peracid to the rated concentration of the mixture.

The method is applicable inter alia to the preparation of stable dilute solutions of peracetic acid.

14 Claims, No Drawings

METHOD OF PREPARING STABLE DILUTE SOLUTIONS OF ALIPHATIC CARBOXYLIC PERACIDS, AND THE RESULTING SOLUTIONS

BACKGROUND OF THE INVENTION

This invention relates to a method of preparing stable dilute solutions of aliphatic carboxylic peracids, inter alia monoperacetic acid.

It is known that solutions of monoperacetic acid prepared from hydrogen peroxide and acetic acid reach equilibrium in accordance with an equation which can be written as follows:

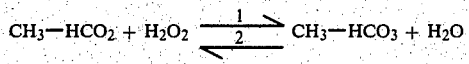

$$CH_3-HCO_2 + H_2O_2 \underset{2}{\overset{1}{\rightleftharpoons}} CH_3-HCO_3 + H_2O$$

The kinetics of this system are relatively slow; the reaction rates are accelerated by strong acids such as sulphuric acid $H_2SO_4$ or phosphoric acid $H_3PO_4$ which, in the present case, act as catalysts. The presence of these strong acids enables the system to move more rapidly towards equilibrium.

It is known, however, that once equilibrium has been reached, the system slowly loses the active oxygen which it contains. This loss results in a slow decrease in the content of peracid and hydrogen peroxide. Stabilizers are added to counteract this phenomenon.

All these phenomena have been demonstrated inter alia by F. K. Greenspan (J. Amer. Chem. Soc., 1946, 68, 907). The author also observed that concentrated solutions are relatively stable, so that peracetic acid can be sold at high concentrations in stabilized solutions. At present, monoperacetic acid is conventionally sold at concentrations of 35–45%.

However, dilute solutions of aliphatic percarboxylic acids which are stable for a prolonged period are required in other applications of monoperacetic acid, e.g. for disinfection and sterilization in medical and food applications.

Various methods have been proposed for obtaining dilute peracetic acid solutions having a concentration between 0.5 and 20%. FMC Corporation's French Pat. No. 1 352 479 relates to a continuous process, by reacting a lower aliphatic acid with hydrogen peroxide in the proportion of 0.3 to 5 mols hydrogen peroxide per mol of acid, in the presence of 5 to 20% of a strong dehydrating acid. French Pat. No. 1 452 484 by the same company relates to a method of producing dilute aqueous solutions of peracetic acid having a concentration of 0.5 to 7% by weight of peracetic acid and a pH of 5.4–7 and free from diacetyl peroxide.

The object of these methods of preparing peracetic acid is to separate the peracetic acid after it has been formed in the reaction mixture. This is either because of the secondary reactions caused by sulphuric acid, $H_2O_2$ and acetic acid, e.g. in epoxidation reactions, or because of the safety problems resulting from the presence of diacetyl peroxide in bleaching operations.

In other applications of peracetic acid, e.g. for disinfection or sterilization, it is unnecessary to separate the product acid from the reaction mixture; solutions of peracetic acid obtained before separation, by the methods described in the preceding patent specifications, can be used for sterilization and disinfection. The same applies to the peracetic acid solutions obtained by Greenspan from 1946 onwards.

More recently, solutions containing 0.5 to 20% of peracid having 2-3 carbon atoms and/or the corresponding aliphatic monocarboxylic acids, 25–40% hydrogen peroxide and 0.05 to 5% by weight of anionic wetting agent in the form of alkylbenzene sulphonate, alkyl sulphate and/or alkane sulphonate, the remainder being water, having been disclosed in French patent application No. 2 321 301. Concentrated solutions containing 0.25 to 10% phosphonic acid or the corresponding water-soluble acid salts are described in French patent application No. 2 321 302; both of these are in the name of Henkel & Co. GmbH.

In any case, if it is desired to manufacture a weak solution of peracetic acid under industrial conditions and even to sell this, it is thought necessary, or at least desirable, that the product solutions must meet the following two basic criteria:

(1) Industrial manufacture of the solutions must be rapid enough to avoid uneconomic storage of the reaction mixtures so as to obtain the desired concentration of peracetic acid. In this connection, the reaction mixture must attain at least 90% of the maximum equilibrium concentration within 48 hours.

(2) The stability of the peracetic acid solution at ambient temperature must be such that the concentration of peracetic acid after storage for 12 months is not below 90% the maximum concentration obtained by the reaction mixture; the maximum concentration may incidentally be different from the rated concentration of the mixture.

In other words, a solution of peracetic acid sold at the rated concentration of 5%, for example, must have a concentration of 5% when sold, 5.55% at maximum concentration and 5% after storage for 12 months at ambient temperature. A process has now been found which meets industrial requirements by solving the inherent difficulties of high-speed production and prolonged storage of dilute solutions of aliphatic carboxylic acids having a concentration of peracid, which does not vary greatly over a prolonged period.

SUMMARY OF THE INVENTION

According to the present invention, there is provided a method of preparing a stable dilute solution of an aliphatic carboxylic peracid, which method comprises a first step in which a concentrated solution of aliphatic peracid is prepared from the corresponding carboxylic acid or anhydride and concentrated hydrogen peroxide in the presence of a small quantity of a strong acid catalyst; and a second step in which the concentrated solution of aliphatic peracid is diluted with a solution containing at least one of the reagents used in the first step, so as to bring the concentration of aliphatic acid to the rated concentration of the mixture. The rated concentration may e.g. be 5% of aliphatic peracid.

DESCRIPTION OF THE PREFERRED EMBODIMENTS

The method can be used to obtain a concentrated solution of aliphatic peracid within a time compatible with industrial manufacture, the solution containing the minimum amount of acid catalyst; if required, the solution can rapidly be brought to equilibrium by raising it to a temperature slightly above ambient temperature. It is preferred to use the minimum amount of strong acid catalyst necessary to achieve equilibrium in the reaction system of the said first step within 48 hours.

In the second step, the concentration of the diluent solution is preferably such that once the concentration of aliphatic carboxylic peracid has been brought to the predetermined rated value, the resulting solution contains a sufficient quantity of reagent for the mixture to develop with time so as to form more of the carboxylic peracid.

The reagent in the diluent solution is either hydrogen peroxide or the starting carboxylic acid, either alone or mixed. Preferably the diluent solution is a solution of hydrogen peroxide.

The amount of reagent, e.g. hydrogen peroxide, in the dilute solution of aliphatic peracid is advantageously such that, during storage of the dilute solution at ambient temperature, (a) the maximum concentration of peracid is at most 10% above the rated concentration of aliphatic peracid (e.g. 5.5% by weight) and (b) the concentration after storage for 12 months is at least equal to the rated concentration of the peracid. Thus, the rated concentration can be the same as the initial concentration, (e.g. 5% by weight).

The effect of diluting the concentrated solution with one of the reagents or a mixture thereof, inter alia with hydrogen peroxide, is to reduce the concentration of acid catalyst, thus considerably slowing down the kinetics of the system. The concentration of the diluent reagent or reagents is chosen so that once dilution has been brought about, the system is no longer at equilibrium, but tends to move in the direction of forming further aliphatic peracid at a very slow rate. The development of the system towards the formation of peracids, though very slow, can compensate for catalytic decomposition for several months of storage.

Advantageously, in the first step of manufacture, the concentrated solution of aliphatic peracid is prepared from the corresponding acid or anhydride, and hydrogen peroxide at a concentration of from 60 to 90% by weight, more preferably of 70 to 85%. In the second step, the concentrated solution of aliphatic peracid is advantageously diluted with hydrogen peroxide at a concentration of from 40 to 70%, more preferably 40 to 50%, by weight.

In the method according to the invention, dilute solutions of an aliphatic carboxylic peracid can be prepared from a monocarboxylic acid containing 2 or 3 carbon atoms or a dicarboxylic acid containing 3 to 5 carbon atoms in the molecule. The acid may, in particular, be acetic acid.

The strong acid catalyst used in preparing the concentrated solution of peracid is preferably a strong mineral acid such as sulphuric or orthophosphoric or an organomineral acid. Advantageously, the catalyst is used in an amount of 0.1 to 5% by weight of the reaction mixture. Preferably the amount of catalyst is 0.2 to 0.5% by weight of the reaction mixture.

In a variant, the dilute solution of aliphatic peracid may contain a stabilizer which, if required, is introduced into the concentrated solution of aliphatic peracid. There are a number of known chemical products, used alone or in mixtures, which have stabilizing properties compatible with the method of this invention. The stabilizer may be, inter alia, dipicolinic acid, sodium stannate, sodium salicylate, hydroquinone or tertiary-butyl hydroxytoluene (BHT).

By means of the present invention, dilute solutions containing between 1 and 20% by weight of carboxylic acid, more particularly of monoperacetic acid, are obtained easily and under very good industrial conditions. Preferably, the concentration of the prepared solutions is from 2 to 5% by weight of carboxylic peracid.

The invention, accordingly, can be used to prepare low-concentration solutions of peracetic acid, which provides an additional safety factor with regard to maintaining the rated concentration of peracetic acid in an industrial product for use e.g., for disinfection or sterilization in medicine or in food. In such cases, the dilute solutions of peracetic acid are sometimes mixed with small quantities of surface-active agents such as alkyl ether sulphates, polyethoxylated non-ionic detergents (e.g. fatty and resin acids), polyethoxylated fatty acids and alkali-metal salts of their sulphated derivatives, alkali-metal salts of sulphated derivatives of polyethoxylated alkyl phenols, fatty acid alkanolamides, or fatty acid esters of saccharose and sucroglycerides.

In view of the fact that the aforementioned industrial product should be of use for a year without risk of loss of efficiency, the safety factor provided by the method of the invention is all the more valuable in that it can compensate for catalytic decomposition of, e.g. the peracetic acid. In industrial manufacture, it is sometimes difficult to make a check for micro-traces of impurities which can catalyze the decomposition of peracetic acid and which may have various origins.

Under such conditions, stabilizers for reducing the kinetic rate of catalytic decomposition may have an effect which fluctuates during industrial manufacture. This may affect dilute solutions of peracetic acid for sale at or near the state of equilibrium and containing the whole proportion of catalyst used for manufacture. If, on the other hand, the catalyst is eliminated by physical and chemical separation processes, there will be a considerable increase in the cost of producing the solution.

The following examples are given by way of non-limitative illustration of the invention.

EXAMPLE 1

A concentrated solution of peracetic acid was prepared by pouring 404g of 90% by weight hydrogen peroxide, with agitation, into a glass balloon flask immersed in a water bath and containing 590.25 g acetic acid mixed with 5 g sulphuric acid and 0.75 g dipicolinic acid. The mixture was kept at between 20° and 22° C. and the concentration of peracetic acid therein reached 45% after about 30 hours.

The mixture then had the following composition, expressed as a percentage by weight:

|  | % by weight |
|---|---|
| Peracetic acid | 45 |
| Acetic acid | 23.6 |
| $H_2O_2$ | 16.1 |
| $H_2O$ | 14.8 |
| $H_2SO_4$ | 0.5 |
| Dipicolinic acid | 750 ppm |

Samples of the concentrated solution were diluted to a tenth of their original concentration with 30, 35, 40, 45 and 50% hydrogen peroxide, respectively, as the diluent, thus almost instantaneously lowering the concentration of peracetic acid in the samples from 45% to 4.5%.

The resulting solutions were stored at ambient temperature for 12 months. The variation (as a percentage by weight) in the content of $H_2O_2$ and peracetic acid (PAA) was periodically measured by analyzing samples from each solution. The results are shown in the following table:

TABLE 1

| Time | 30% $H_2O_2$ | | 35% $H_2O_2$ | | 40% $H_2O_2$ | | 45% $H_2O_2$ | | 50% $H_2O_2$ | |
| --- | --- | --- | --- | --- | --- | --- | --- | --- | --- | --- |
| | $H_2O_2$ | PAA | $H_2O_2$ | PAA | $H_2O_2$ | PAA | $H_2O_2$ | PAA | $H_2O_2$ | PAA |
| 0 | 28.7 | 4.5 | 33 | 4.5 | 37.6 | 4.5 | 42.1 | 4.5 | 46.6 | 4.5 |
| 1 month | 28.5 | 3.7 | 32.8 | 4.2 | 37.5 | 4.6 | 41.6 | 4.9 | 45.3 | 5.3 |
| 2 months | 28.5 | 3.6 | 32.8 | 4.2 | 37.5 | 4.8 | 41.4 | 5.2 | 45.0 | 5.7 |
| 5 months | 28.5 | 3.5 | 32.7 | 4.1 | 37.4 | 4.8 | 41.3 | 5.1 | 44.8 | 5.6 |
| 7 months | 28.4 | 3.4 | 32.6 | 4.0 | 37.2 | 4.8 | 41.3 | 5.0 | 44.6 | 5.5 |
| 10 months | 28.4 | 3.4 | 32.4 | 4.0 | 36.8 | 4.7 | 41.2 | 4.9 | 44.4 | 5.2 |
| 12 months | 28.3 | 3.3 | 32.3 | 3.9 | 36.5 | 4.7 | 41.1 | 4.8 | 44.3 | 5.1 |

In all the solutions, there was a continuous and progressive decrease in the $H_2O_2$ content. There was also a continuous and progressive decrease in the content of peracetic acid in the solutions diluted with 30 and 35% $H_2O_2$. In the case, however, of solutions diluted with 40, 45 and 50% $H_2O_2$, there was an increase followed by a decrease in the content of peracetic acid.

As the results in Table 1 show, the increase in the content of peracetic acid occurs over several months of storage at ambient temperature. The solutions under study contained 0.05% $H_2SO_4$.

The following are the variations ($\Delta\%$) in the maximum concentration and final concentration relative to the initial concentration, for each solution:

TABLE 2

| | Maximum concentration initial concentration $\Delta\%$ | Final concentration/ initial concentration $\Delta\%$ |
| --- | --- | --- |
| $H_2O_2$ 40% | 6.7 | 4.4 |
| $H_2O_2$ 45% | 15.6 | 6.6 |
| $H_2O_2$ 50% | 26.7 | 13.3 |

The results in Table 2 show that the peracetic acid solution obtained by dilution with 40% $H_2O_2$ shows the minimum variation in the concentration of peracetic acid during 12 months' storage. This solution was the only one which met the previously-defined stability criterion. Solutions obtained by dilution with 45 or 50% $H_2O_2$ show variations in concentration above 10%, but the concentration of peracetic acid after 12 months' storage was nevertheless greater than the initial concentration.

EXAMPLE 2

By way of comparison, measurements were made of the progressive variation in a solution of low-concentration peracetic acid prepared in conventional manner from glacial acetic acid and $H_2O_2$ in the presence of a strong acid catalyst and mixed with a stabilizer. The solution was prepared from 56 g glacial acetic acid plus 1.04 g $H_2SO_4$ mixed with 662.5 g of 70% $H_2O_2$ and 321.5 g de-ionized water. The resulting mixture contained 0.1% $H_2SO_4$; 75 ppm dipicolinic acid was added thereto.

The progressive variation in the content of peracetic acid was periodically measured by analyzing samples of the mixture, stored at ambient temperature. The results are given in Table 3 below:

TABLE 3

| Time | Peracetic Acid |
| --- | --- |
| 8 days | 2.3% |
| 15 days | 3.2% |
| 21 days | 3.5% |
| 30 days | 3.7% |

The results in Table 3 show that, at ambient temperature and with 0.1% $H_2SO_4$, 92% of equilibrium is obtained after 21 days and 97% of equilibrium after 30 days. These results show the considerable difference between the kinetics of dilute peracetic acid solutions and of concentrated peracetic acid solutions. The kinetics are also dependent on the concentration of catalysts, strong acid (e.g. $H_2SO_4$) and temperature.

EXAMPLE 3

The effect of the concentration of catalyst and the temperature was examined. A peracetic acid solution was prepared by the same method as in Example 2 above from glacial acetic acid and $H_2O_2$ (70% by weight). At the start, the mixture contained 1.5 mols glacial acetic acid per mole of 100% $H_2O_2$; and 75 ppm dipicolinic acid. A number of mixtures were prepared with increasing concentrations of $H_2SO_4$, i.e. 0.1%, 0.3%, 0.5%, 0.75% and 1%. Two sets of identical mixtures were stored, one at 20° C. and the other at 30° C. Each mixture was measured to find the time taken for the concentration of peracetic acid to reach 35% in the mixture. The results are given below in Table 4.

TABLE 4

| The time taken to obtain 35% peracetic acid in the mixture | | | | | |
| --- | --- | --- | --- | --- | --- |
| Storage temperature of mixture | % $H_2SO_4$ | | | | |
| | 0.1 | 0.3 | 0.5 | 0.75 | 1 |
| 20° C. | 110 h | 42 h | 21 h | 15 h | 10 h |
| 30° C. | 48 h | 19 h | 9 h | 6.5 h | 5 h |

Table 4 shows (a) that the reaction rates are increased substantially by a factor of 2 between 20° C. and 30° C. and (b) they are multiplied progressively as the $H_2SO_4$ concentration increases from 0.1% to 1%, the factor being about 2 when the change in concentration is from 0.1 to 0.3%, from 0.3% to 0.5%, or from 0.5 to 1%. Thus the reaction rates vary by a factor of approximately 10, when the $H_2SO_4$ concentration increases from 0.1 to 1%. Table 4 shows, for example, that a 35% solution of peracetic acid with 0.1% $H_2SO_4$ can be prepared in 48 hours provided the reaction mixture is maintained at 30° C. The 35% solution of peracetic acid can be diluted with 42% $H_2O_2$, for example, to give a solution containing 5% peracetic acid and only 0.014% $H_2SO_4$ (dilution to one-seventh).

What is claimed is:

1. A method of preparing a dilute solution, containing a rated concentration between 1 and 20% by weight, of an aliphatic carboxylic peracid with a stable concentration titer in time, notwithstanding the possible presence of trace amounts of decomposition catalysts, comprising the steps of:

preparing a concentrated solution of aliphatic peracid from the corresponding carboxylic acid or anhydride and hydrogen peroxide in a concentration of between 60 and 90% in the presence of the substantially minimal amount of a strong acid catalyst necessary to obtain equilibrium of the system in a maximum period of 48 hours; and diluting the concentrated solution of aliphatic peracid, prepared in said preparing step, with a solution containing at least one of the reagents used in said preparing step in an amount and concentration sufficient to bring the concentration of aliphatic peracid at least to the rated concentration of the mixture and such that (a) the maximum concentration of peracid during storage at ambient temperature is at most 10% above the rated concentration of peracid and (b) the concentration after storage for 12 months is at least equal to the rated concentration of aliphatic peracid.

2. A method, according to claim 1, wherein a stabilizer is introduced into the concentrated solution of aliphatic peracid in said preparing step.

3. A method according to claim 1, wherein the strong acid catalyst used in the preforming step is a strong mineral acid.

4. A method according to claim 3, wherein the strong acid catalyst is selected from sulphuric and orthophosphoric acids and organo-mineral acids and is used in a proportion of 0.1 to 5% by weight of the reaction mixture.

5. A method according to claim 4, wherein the said acid is used in a proportion of 0.2 to 0.5% by weight of the reaction mixture.

6. A method according to claim 1, wherein in the preparing step, the carboxylic acid is selected from monocarboxylic acids containing 2 or 3 carbon atoms in the molecule and di-carboxylic acids containing 3-5 carbon atoms.

7. A method according to claim 1, wherein, in said preparing step, said hydrogen peroxide is at a concentration of 70 to 85% by weight.

8. A method according to claim 1, wherein, in the diluting step, the concentrated solution of aliphatic peracid is diluted with hydrogen peroxide at a concentration of from 40 to 70% by weight.

9. A method according to claim 8, wherein, in the diluting step, the hydrogen peroxide is used at a concentration of 40 to 50% by weight.

10. A method in accordance with claim 1 wherein said acid is present in an amount of 0.1–5% by weight in relation to said reaction mixture.

11. A method in accordance with claim 1 wherein, in said preparing step, said strong acid is a strong inorganic acid in an amount of 0.2–0.5% by weight in relation to the reaction mixture, and, in said diluting step, the concentrated solution of aliphatic peracid is diluted with hydrogen peroxide at a concentration of 40–50% by weight.

12. A method in accordance with claim 1, wherein said strong inorganic acid is mineral acid.

13. A method in accordance with claim 1, wherein said aliphatic carboxylic peracid is peracetic acid; wherein, in said preparing step, said corresponding carboxylic acid or anhydride is acetic acid or anhydride and said strong acid catalyst is present in an amount of 0.1–0.5% by weight in relation to the reaction mixture; and wherein, in said diluting step, the concentrated peracetic acid solution prepared in said preparing step is diluted with hydrogen peroxide at a concentration of 40–70%.

14. A method in accordance with claim 1, wherein the aliphatic carboxylic peracid is peracetic acid and the rated concentration of the final product is 2–5% by weight; wherein, in said preparing step said corresponding carboxylic acid or anhydride is acetic acid, said hydrogen peroxide is present in a concentration of 70–90% and said strong acid catalyst is sulfuric acid present in an amount of 0.2–0.5% by weight in relation to said reaction mixture; and wherein, in said diluting step, the concentrated peracetic acid solution prepared in said preparing step is diluted with hydrogen preoxide at a concentration of 40–70%.

* * * * *